(12) United States Patent
Jaroszeski et al.

(10) Patent No.: US 7,713,740 B2
(45) Date of Patent: May 11, 2010

(54) METHOD OF USING ELECTRIC FIELDS TO FACILITATE THE ENTRY OF MOLECULES INTO CELLS IN VIVO

(75) Inventors: Mark J. Jaroszeski, Wesley Chapel, FL (US); Richard Gilbert, Tampa, FL (US); Richard Heller, Temple Terrace, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 09/939,518

(22) Filed: Aug. 24, 2001

(65) Prior Publication Data

US 2003/0044985 A1 Mar. 6, 2003

(51) Int. Cl.
*C12N 15/87* (2006.01)
*A61N 1/30* (2006.01)

(52) U.S. Cl. .......................... 435/461; 604/20

(58) Field of Classification Search .............. 435/173.6, 435/461, 455; 604/19, 501, 20; 607/74, 607/1

See application file for complete search history.

(56) References Cited

U.S. PATENT DOCUMENTS

| 6,055,453 | A  | * | 4/2000 | Hofmann et al. | 604/21 |
| 6,241,701 | B1 |   | 6/2001 | Hofmann        |        |
| 6,678,558 | B1 | * | 1/2004 | Dimmer et al.  | 607/3  |
| 6,800,484 | B2 | * | 10/2004 | Nolan et al.  | 435/461 |

FOREIGN PATENT DOCUMENTS

WO   WO 9843702 A2 * 10/1998

* cited by examiner

*Primary Examiner*—J. E Angell
(74) *Attorney, Agent, or Firm*—Michael M. McGaw; Smith & Hopen, P.A.

(57) ABSTRACT

A method for facilitating a delivery of a molecule into an interior space of a cell includes the steps of introducing a molecule into a target tissue comprising a cell and applying a substantially continuous low-level electric field to the target tissue. The field is applied for a duration sufficient to effect a change in porosity the cell of the target tissue sufficient to facilitate an entry of a desired molecule into an interior of the cell.

10 Claims, No Drawings

METHOD OF USING ELECTRIC FIELDS TO FACILITATE THE ENTRY OF MOLECULES INTO CELLS IN VIVO

BACKGROUND OF THE INVENTION

1. Field of the Invention

This invention relates to the use of an electric field to effect the delivery of a molecule to a target tissue site and facilitate the uptake of a molecule by a cell.

2. Description of Related Art

Most therapeutic molecules require delivery to a living cell by some means in order to effect a response. Standard therapies include oral administration or other techniques to introduce a treatment molecule into the system. However, even with a therapeutic molecule in the vicinity of a cell, the cell membrane can partially or completely block the uptake of that molecule into the cell itself. To overcome this, many methods have been developed; one such method is the use of electric fields to facilitate passage of the molecules from the extracellular space to the intracellular space.

Scientific research has led to the current understanding that exposure of cells to intense electric fields for brief periods of time temporarily destabilizes membranes. This effect has been described as a dielectric breakdown due to an induced transmembrane potential, and was termed "electroporation," or "electropermeabilization," because it was observed that the molecules that do not normally pass through the membrane gain intracellular access after the cells were treated with electric fields. The porated state was noted to be temporary, with the cells typically remaining in a destabilized state on the order of a few minutes after the cessation of the electrical fields.

The physical nature of electroporation makes it universally applicable. A variety of in vivo procedures utilize this type of treatment to gain temporary access to the cytosol. These include the delivery of drugs to cells within tissues and the delivery of DNA to cells within tissues. A notable example of loading molecules into cells in vivo is electrochemotherapy. The procedure utilizes a drug combined with electric pulses as a means for loading tumor cells with an anticancer drug, and has been performed in a number of animal models and in clinical trials (see, for example, Heller et al., *Cancer* 77, 964-71, 1996). Also, plasmid DNA has been loaded into rat liver cells (Heller et al., *FEBS Lett.* 389, 225-28, 1996), murine tumors (Niu et al., *Cancer Research* 59, 5059-63, 1999), rat hepatocellular carcinomas (Heller et al., *Gene Therapy* 7, 826-29, 2000), and murine skin in vivo [Heller et al., *DNA and Cell Biology* 20(1), 21-26, 2001].

The loading of molecules by electroporation in vivo is typically, but not necessarily, carried out by first exposing the cells (located within a tissue) of interest to the molecule to be loaded. This is accomplished by placing the molecules of interest into the extracellular space by injection, jet injection, transdermal delivery, infusion into tissue or blood vessel, or other means known in the art. The cells are then exposed to electric fields by administering one or more direct current pulses. Pulsed electric fields are normally applied using an electrical generator and electrodes that contact or penetrate a region of tissue, which allows electrical energy to be transmitted to the cells of interest. Electrical treatment is typically, but not necessarily, conducted in a manner that results in a temporary membrane destabilization with minimal cytotoxicity.

The intensity of electrical treatment is described by the magnitude of the applied electric field. This field is defined as the voltage applied to the electrodes divided by the distance between the electrodes. Generally, electric field strengths ranging from 100 to 5000 V/cm have been used; this range has been dictated by the need to interfere with the cell membrane to effect the uptake of the molecular species desired. In addition, the field strength is also a function of the type of tissue to be treated, with some requiring higher fields owing to their specific natures.

High field strengths, 100 V/cm and greater, were used exclusively in the past. The duration of the applied fields is an important factor, and the relationship between field strength and duration is critical. The current state of the art utilizes high electric field strengths to effect the membrane change and requires pulse durations that are very brief in order to achieve molecular delivery. The concept of very long pulse durations (greater than 100 ms) has heretofore never been used with respect to the field strength, enabling in vivo molecular delivery using almost insignificant electric fields. In fact, the converse was held to be true by practitioners of the art; operating parameters with short-duration high fields being held as the only way to achieve electroporation. The pulsed electric fields used for molecule delivery are generally rectangular in shape; however, exponentially decaying pulses and bipolar pulses have also been used. Molecular loading has been performed with pulse widths ranging from microseconds to milliseconds. The number of pulses delivered typically has ranged from one to eight, with multiple pulses being applied during the course of a treatment.

Work related to the manipulation of the parameters influencing electroporation devices has been the subject of many articles and patents. One such patent, U.S. Pat. No. 6,241,701 to Hoffmann, describes electric field intensities ranging from 25 to 1300 V/cm with times or pulse widths ranging from 10 µs to about 100 ms. The effectiveness of these ranges is described as a correlation between high fields for short duration versus low fields with a preferred longer pulse width. From the statements contained in Hoffmann, one would be led to manipulate the parameters equally with respect to each other, since they are described as being equal in importance. There is no suggestion to vary one parameter, namely, the pulse width, to be greater in an nonlinear fashion with respect to the field strength; in addition, there is no teaching to extend the pulse width to anytime greater than 100 ms.

SUMMARY OF THE INVENTION

It is therefore an object of the invention to provide a system and method for facilitating a delivery of a molecule into an interior space of a cell.

It is a further object to provide such a system and method incorporating low electric fields and long pulse durations.

These and other objects are achieved by the present invention, a first aspect of which comprises a method for facilitating a delivery of a molecule into an interior space of a cell. The method comprises the steps of introducing a molecule into a target tissue comprising a cell and applying a substantially continuous low-level electric field to the target tissue. The field is applied for a duration sufficient to effect a change in porosity in the cell of the target tissue sufficient to facilitate an entry of a desired molecule into an interior of the cell.

The invention further comprises a system for facilitating a delivery of a molecule into an interior space of a cell. The system comprises means for introducing a molecule into a target tissue comprising a cell and means for applying a substantially continuous low-level electric field to the target tissue. The applying means comprises means for applying the field for a duration sufficient to effect a change in porosity the cell of the target tissue sufficient to facilitate an entry of a desired molecule into an interior of the cell.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read.

DETAILED DESCRIPTION OF THE PREFERRED EMBODIMENTS

A description of the preferred embodiments of the present invention will now be presented.

As described above, the electric field strength and pulse duration of the instant invention provide for a facilitation of the delivery of a molecule to a target cell, as effected by a low-voltage electric field with increasing application times or pulse widths. For example, within some field strength ranges, the application time or pulse width will be orders of magnitude higher than previously described, although this is not intended as a limitation.

For the purpose of this invention, a pulsed electric field is defined as the electric field resulting from an application of an electric waveform such as rectangular or exponentially decaying waveform. The pulsed electric fields comprise a variety of shapes, including, but not limited to, square, rectangular, exponentially decaying, exponentially increasing, bipolar, or sinusoidal pulses, or any combination of the foregoing and including nongeometrically characterizable shapes, with or without AC and DC offset (bias) voltages. The foregoing list of waveforms also is intended to include waveforms that can be characterized by mathematical functions or mathematical approximations.

The characteristics of the field used to facilitate the entry of the molecules into the target cell include field strengths between 1 mV/cm and 200 V/cm, applied as pulses of substantially continuous energy. The duration of the pulse ranges from 0.1 s to 20 minutes, with 100 ms to 100 s duration comprising a preferred range. A single pulse may be applied or a plurality of sequential pulses, either of the same magnitude or differing magnitudes of duration and field strength. A preferred pulse duration range has been found to be actually approximately exponentially greater than those suggested by the prior art in some ranges, and greatly exceeds any known to have been reported to date. In fact, the present inventors have discovered that by using a longer pulse duration, the field strength needed to effect facilitation of molecular delivery may be significantly lowered. As a result, fewer deleterious effects of the procedure are experienced, since the electric field imposition is more a function of time rather than field strength.

The tissues to which this method may be applied include, but are not intended to be limited to, skin, tumor, skeletal muscle, smooth muscle, blood, blood vessel, brain, lymph, liver, pancreas, bone, colon, small intestine, cardiac, lung, breast, testes, prostate, and cornea. In fact, any living species that uses gas transfer in its metabolic processes may be used as a target tissue, including, but not limited to: animals, plants, fish, various insect species, reptiles, etc. The magnitude of the electric fields applied are selected based on the susceptibility of the particular tissue to the pulses, and the corresponding pulse durations are a function of the resistivity of the type of tissue to temporary electrical damage. Representative parameters for a few types of tissue are contained in Table 1.

TABLE 1

| Tissue | Range of Field Parameters | Preferred Duration Range | Preferred Strength Range |
|---|---|---|---|
| Muscle | 1 µs–100 s<br>1 mV/cm–10,000 V/cm | 100 ms–10 s | 1 mV/cm–400 V/cm |
| Skin | 1 µs–100 s<br>1 mV/cm–10,000 V/cm | 100 ms–10 s | 1 mV/cm–500 V/cm |
| Tumor | 1 µs–100 s<br>1 mV/cm–10,000 V/cm | 100 ms–10 s | 1 mV/cm–800 V/cm |

As shown in Table 1, the pulse width is believed to comprise a critical factor in the method of the present invention.

The means for introducing the molecule of interest into the target tissue may comprise a technique selected from a group consisting of traditional syringe injection, jet injection, oral dosing, or other means as known in the art. In addition, the molecule of interest may also be caused to move to the target tissue by means of other electric pulses or by other means known in the art. The molecule of interest may also be dissolved, suspended, or emulsified in an appropriate carrier.

A subject molecule desired to be delivered may be selected for entry into the cells for a plurality of reasons, including, but not intended to be limited to, genetically modifying cells, inducing the secretion of a substance locally or systemically, inducing the production of a substance within a cell, inducing the production of a substance that is embedded in the membrane, or any other purpose known in the art.

The system and method of the invention is further described with the use of the following examples of the expression of luciferase in skin tissue of mice and the gastrocnemius muscle of mice.

Example 1

A plasmid (pCMVLuc), constructed of DNA with a cDNA insert that codes for the enzyme lucerifase, was propagated in the bacterium E. coli and then purified using a Quiagen plasmid preparation kit (Quiagen, Valencia, Calif.). The plasmid was suspended in saline at a concentration of 2 mg/ml for use in the experiment. A 50-ml quantity of the plasmid was injected intradermally into the flanks of C57B1/6 mice. Immediately after injection, four surface electrodes were placed on adjacent sides of the injection site and a series of discrete electric pulses with a field strength of 10 V/cm were applied to the skin so that current passed through the injected tissue. The duration of these pulses was 1 s. The treated skin was surgically harvested 48 h later and analyzed using standard methods for luciferase expression. These results, expressed in relative light units, are shown in Table 2.

TABLE 2

Luciferase Expression as a Function of Treatment Conditions

| Treatment Conditions | Mean Magnitude of Luciferase Expression |
|---|---|
| Injection only | 1,473,712.94 |
| Injection followed by electric field treatment of 10 V/cm, 1 s duration | 7,360,666.54 |

The results of Table 2 indicate that skin treated with the plasmid DNA followed by electric pulses evinced a lucerifase expression that was approximately 5 times higher than samples that were treated with the plasmid alone, clearly indicating that low-electric-field-strength pulses with a very long duration facilitated the entry of plasmid DNA into the interior of the skin cells. The duration of the pulses used for these samples was tenfold higher than the maximum duration suggested in the known literature of the art.

Example 2

The procedures in Example 1 were repeated to deliver the luciferase coding plasmid to skin again using different electrical conditions. The results, expressed in relative light units, are shown in Table 3.

TABLE 3

Luciferase Expression as a Function of Treatment Conditions

| Treatment Conditions | Mean Magnitude of Luciferase Expression |
| --- | --- |
| Injection of plasmid only | 1,346,831.25 |
| Injection of plasmid followed by electrical treatment 50 V/cm, 200 ms duration | 5,077,201.00 |
| Injection of plasmid followed by electrical treatment 100 V/cm, 200 ms duration | 59,529,447.97 |

The results indicate that using pulses with a field strength of 50 V/cm and a duration of 200 ms yields a luciferase expression that was approximately 3.5 times that of the control animals that received only an injection of the plasmid (no fields were applied). Samples that received 100-V/cm pulses with 200-ms duration had 44 times more luciferase expression than the control samples. This example indicates that pulse durations well above the highest disclosed by the art have utility for facilitating the delivery of molecules to cells of a target tissues.

Example 3

Plasmid DNA coding for luciferase has also been delivered to murine gascrocnemius muscles. This was carried out by injecting a 50-µl quantity of the plasmid DNA (2 mg/ml) directly into the muscles. A penetrating electrode was then inserted into the muscle tissue that was infused with the plasmid DNA solution and pulsed electric fields were applied. 48 h after this treatment, the muscles were excised and analyzed for luciferase using standard methods. The resulting data, expressed in relative light units, are given in Table 4.

TABLE 4

Luciferase Expression in Muscle

| Treatment Conditions | Mean Magnitude of Luciferase Expression |
| --- | --- |
| Injection only | 1,393,829 |
| Injection, followed by electrical treatment of 20-V/cm, 1-s duration | 484,134,407 |

The results obtained indicated that muscle treated with the plasmid DNA followed by electric pulses expressed luceriſase approximately 347 times higher than samples that were not treated with the electric pulses. This indicates that the entry of plasmid DNA to the interior of a cell can be effected by long-pulse-duration low-field-strength electrical conditions.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the method illustrated and described herein are by way of example, and the scope of the invention is not limited to the exact details disclosed.

Having now described the invention, the construction, the operation and use of preferred embodiments thereof, and the advantageous new and useful results obtained thereby, the new and useful methods, and reasonable equivalents thereof obvious to those skilled in the art, are set forth in the appended claims.

What is claimed is:

1. A method for facilitating the delivery of a desired molecule into a target tissue consisting essentially of the steps of:
   introducing a molecule into a target tissue comprising a cell;
   applying an electric field to the target tissue, the application of the electric field consisting of a single continuous electric field in the range of 1 mV/cm to 200 V/cm applied for a duration of 200 ms to 20 minutes; and
   effecting a change in porosity of the cell of the target tissue in response to the application of the electric field, the change in porosity sufficient to facilitate entry of a desired molecule into an interior of the cell.

2. The method recited in claim 1, wherein the duration of the applying step is in a range of 200 ms to 100 sec.

3. The method recited in claim 1, wherein the electric field is a pulse selected from a group of waveforms consisting of square, rectangular, exponentially decaying, exponentially increasing, bipolar, and sinusoidal; waveforms having a non-geometrically characterizable shape; waveforms characterizable by a mathematical function; waveforms characterizable by a mathematical approximation; waveforms with at least one of an AC or a DC offset signal; and waveforms without an AC or a DC offset signal.

4. The method recited in claim 1, wherein the introducing step comprises the step selected from a group consisting of syringe injection, jet injection, oral dosing, transdermal delivery, infusion into tissue, and infusion into a blood vessel.

5. The method recited in claim 1, wherein the target tissue is selected from a group consisting of skin, tumor, muscle, blood, blood vessel, brain, lymph, liver, pancreas, bone, colon, cardiac, lung, breast, testes, cornea, prostate, and intestine.

6. A method for facilitating the delivery of a desired molecule into a target tissue comprising the steps of:
   introducing a molecule into a target tissue comprising a cell; and
   applying a continuous electric field in the range of 1 mV/cm to 200 V/cm to the target tissue for a duration of 200 ms to 20 minutes to effect a change in porosity of the cell of the target tissue sufficient to facilitate entry of a desired molecule into an interior of the cell.

7. The method recited in claim 6, wherein the duration of the applying step is in a range of 200 ms to 100 sec.

8. The method recited in claim 6, wherein the electric field is a pulse selected from a group of waveforms consisting of square, rectangular, exponentially decaying, exponentially increasing, bipolar, and sinusoidal; waveforms having a non-geometrically characterizable shape; waveforms characterizable by a mathematical function; waveforms characterizable by a mathematical approximation; waveforms with at least one of an AC or a DC offset signal; and waveforms without an AC or a DC offset signal.

9. The method recited in claim 6, wherein the introducing step comprises the step selected from a group consisting of syringe injection, jet injection, oral dosing, transdermal delivery, infusion into tissue, and infusion into a blood vessel.

10. The method recited in claim 6, wherein the target tissue is selected from a group consisting of skin, tumor, muscle, blood, blood vessel, brain, lymph, liver, pancreas, bone, colon, cardiac, lung, breast, testes, cornea, prostate, and intestine.

* * * * *